United States Patent
Gilligan et al.

(10) Patent No.: US 10,597,628 B2
(45) Date of Patent: Mar. 24, 2020

(54) DEVICE FOR RECEIVING FLUID

(71) Applicant: Blacktrace Holdings Ltd., Royston, Hertfordshire (GB)

(72) Inventors: Mark Gilligan, Royston (GB); Tim Atkins, Royston (GB); Andrew Lovatt, Cambridge (GB); Joe Fiabane, Somersham (GB); Philip Homewood, Enfield (GB); Mike Hawes, Benington (GB)

(73) Assignee: Blacktrace Holdings Ltd., Royston, Hertfordshire (GB)

( * ) Notice: Subject to any disclaimer, the term of this patent is extended or adjusted under 35 U.S.C. 154(b) by 254 days.

(21) Appl. No.: 15/728,648

(22) Filed: Oct. 10, 2017

(65) Prior Publication Data
US 2018/0105789 A1   Apr. 19, 2018

(30) Foreign Application Priority Data
Oct. 13, 2016 (GB) .................................. 1617354.4

(51) Int. Cl.
*C12M 1/33* (2006.01)
*B01F 15/02* (2006.01)
(Continued)

(52) U.S. Cl.
CPC ........... *C12M 45/02* (2013.01); *B01F 3/0807* (2013.01); *B01F 3/0853* (2013.01);
(Continued)

(58) Field of Classification Search
CPC ...... C12M 45/02; C12M 23/16; C12M 27/02; C12M 29/00; B01F 15/0258;
(Continued)

(56) References Cited

U.S. PATENT DOCUMENTS

| 3,539,155 A | 11/1970 | Agranat | |
|---|---|---|---|
| 2004/0234566 A1* | 11/2004 | Qiu | A61K 8/06 424/401 |

(Continued)

FOREIGN PATENT DOCUMENTS

| EP | 0 870 541 A2 | 10/1998 |
| WO | WO 2012/084615 A1 | 6/2012 |

OTHER PUBLICATIONS

Communication with European Search Report, EP Application No. 17194526.4, dated Mar. 15, 2018, 7 pp.

*Primary Examiner* — Lore R Jarrett
(74) *Attorney, Agent, or Firm* — Myers Bigel, P.A.

(57) ABSTRACT

A device (10), for receiving fluid, having a block (12) which comprises: a chamber (14) comprising a top and a bottom; and a chamber outlet (20) at the bottom of the chamber (14). The block (12) further comprises a magnetic stirrer (30) suspended in the chamber (14), wherein the magnetic stirrer (30) terminates above the bottom of the chamber (14), and is rotatably supported inside the chamber (14). The block (12) further comprises a microchannel (26) fluidly connected to the chamber (14) via the chamber outlet (20). The microchannel (26) may be fluidly connected to a downstream reservoir (24), and an upstream reservoir (22). The device (10) is suited for mixing a bead/cell suspension and an oil-based fluid in the microchannel (26) such that they form an emulsion which comprises a plurality of droplets, wherein at least one of the droplets encapsulates a bead/cell.

5 Claims, 5 Drawing Sheets

(51) Int. Cl.
  *B01F 13/00* (2006.01)
  *B01F 3/08* (2006.01)
  *B01F 13/08* (2006.01)
  *B01F 17/00* (2006.01)
  *C12M 3/06* (2006.01)
  *C12M 1/06* (2006.01)
  *C12M 1/00* (2006.01)

(52) U.S. Cl.
  CPC ...... *B01F 13/0059* (2013.01); *B01F 13/0062* (2013.01); *B01F 13/0827* (2013.01); *B01F 15/0238* (2013.01); *B01F 15/0258* (2013.01); *B01F 17/00* (2013.01); *C12M 23/16* (2013.01); *C12M 27/02* (2013.01); *C12M 29/00* (2013.01); *B01F 2215/0037* (2013.01)

(58) Field of Classification Search
  CPC .............. B01F 15/0238; B01F 13/0062; B01F 3/0853; B01F 13/0059; B01F 3/0807; B01F 17/00; B01F 13/0827; B01F 2215/0037; B01L 3/502715; B01L 3/502784; B01L 3/502738; B01L 3/502746; B01L 2400/06; B01L 2400/0487; B01L 2300/0874; B01L 2300/0867; B01L 2300/0816; B01L 2200/12; B01L 2200/0621; B01L 2300/14; B01L 2300/0887; B01L 2200/141; B01L 2200/0689; F16K 99/0021; F16K 2099/0084
  See application file for complete search history.

(56) References Cited

U.S. PATENT DOCUMENTS

| | | | |
|---|---|---|---|
| 2005/0221339 A1* | 10/2005 | Griffiths | B01F 5/0655 |
| | | | 435/6.11 |
| 2005/0277187 A1 | 12/2005 | Johnson et al. | |
| 2006/0120213 A1* | 6/2006 | Tonkovich | B01F 3/0807 |
| | | | 366/144 |
| 2006/0199260 A1 | 9/2006 | Zhang et al. | |
| 2008/0031088 A1 | 2/2008 | Ukita | |
| 2011/0104747 A1* | 5/2011 | Pollack | B01F 13/002 |
| | | | 435/40.5 |
| 2015/0298091 A1* | 10/2015 | Weitz | B01J 19/0046 |
| | | | 506/16 |

* cited by examiner

DEVICE FOR RECEIVING FLUID

RELATED APPLICATION

This application claims priority from Great Britain Patent Application No. 1617354.4, filed on Oct. 13, 2016, the disclosure of which is hereby incorporated herein by reference in its entirety.

The present invention relates to a device for receiving fluid. Preferably the device is for receiving, processing and analysing biological cells/beads.

BACKGROUND RELATING TO THE PRIOR ART

Microfluidic devices have been widely used for receiving, processing and analysing biological cells/beads. The size of the channels in these devices, typically 1-1000 microns in diameter, allows accurate manipulation and control of individual cells.

An example prior art setup for processing and analysing biological cells/beads is shown in FIG. 1.

Prior to use, cells/beads are typically held in a suspension which is located in a reservoir. To prevent the cells/beads from this suspension from settling whilst in the reservoir, there is the need to ensure that the suspension is constantly stirred. To prevent such settling, a 'bar' stirrer is located at the base of the reservoir, which can rotate to keep the contents of the reservoir stirred.

The cell/bead suspension can be pumped out of the reservoir by applying pressured gas into the top of the reservoir. From the reservoir, the suspension is pumped into a tube which leads to a microchannel located in a microfluidic device. Inside the microfluidic device, the suspension is passed through the microchannel to a mixing point.

At the mixing point, the suspension is mixed with a further fluid(s), such as a different bead/cell suspension, and/or an oil-based fluid. Each further fluid is similarly pumped to the mixing point in the microfluidic device from a respective reservoir/tube/microchannel arrangement.

Downstream of the mixing point, the microchannel inside the microfluidic device delivers the mixed fluids to an output tube located off the microfluidic device. This tube then leads to an output reservoir where the mixed fluids are stored. The output reservoir is also located off the microfluidic device.

One disadvantage of the above setup is the use of the 'bar' stirrer which rotates at the base of the cell/bead suspension reservoir. This rotation causes damage to the cells located between the reservoir and the rotating tar' stirrer, due to cells getting caught between the two surfaces, and also due to high shear forces in this region.

Since cells/beads tend not stay in suspension for long, and tend to settle out (due to differences in density between the cells/beads and the aqueous medium in which they are suspended), a further disadvantage of the above setup is that clogging, and thus blockages, tends to occur in the tubes and connectors between the reservoirs and the microfluidic device.

The present invention seeks to solve the above mentioned problems, and others.

SUMMARY OF THE INVENTION

According to the present invention, there is provided a device for receiving fluid, the device comprising a block which comprises:

a chamber comprising a top and a bottom; and comprising a chamber outlet at the bottom of the chamber;
a magnetic stirrer suspended in the chamber, wherein the magnetic stirrer terminates above the bottom of the chamber, and is rotatably supported inside the chamber; and
a microchannel fluidly connected to the chamber via the chamber outlet.

Since the above device uses a magnetic stirrer suspended in the chamber, the device can hold and stir cell/beads suspensions with minimal damage to any cells/beads located therein. In addition, by having the chamber and the microchannel all located in a block, this removes the need for any intermediary tubes and connectors between the chamber and the microchannel. The above mentioned problem of clogging in such tubes is therefore inhibited.

Preferably, the chamber has a fluid capacity of between 100 μl-100 ml.

Preferably, the chamber comprises an aperture towards the top of the chamber; wherein the magnetic stirrer is suspended in the chamber via the aperture. In this case, rather than rely solely on a magnetic force to support the magnetic stirrer, the aperture can be used to provide additional support to the magnetic stirrer.

The magnetic stirrer may be arranged to rest on a first side of the aperture. In this case, the magnetic stirrer may comprise at least one protrusion which is operable to engage with a second side of the aperture. In this way, the magnetic stirrer can be conveniently secured inside the chamber.

Preferably, the magnetic stirrer snap-fits in the aperture. In this way, once the stirrer has been inserted in the chamber, the snap fit prevents the stirrer from being removed.

The chamber may be substantially cylindrical.

In some cases, a gasket may be connectable to the block to create an air-tight seal between the block and the gasket. In this case, to allow easier maintenance and access inside the device, preferably the gasket is detachable from the block.

Where a gasket is present, the device may further comprise a manifold engageable against the gasket. In this case, the gasket may be operable to be compressed between the manifold and the block. Preferably, such compression creates an air-tight-seal between the gasket and the block. In this way, the chamber inside the block can be more conveniently pressurised, in use, as required.

In cases where there is a manifold, the manifold may comprise a drive magnet which is coupleable with the magnetic stirrer. In such cases, the drive magnet may be located within a recess of the manifold.

The chamber may comprise an enlarged portion toward the top of the chamber. This portion allows a fluid to be more easily poured/pipetted into the chamber.

In this case, and when then device has a gasket, the gasket may comprise a fluid/gas inlet fluidly connected to the enlarged portion, wherein the fluid inlet is offset from the rotation axis of the magnetic stirrer. The above arrangement provides a convenient way for introducing fluid/gas into the chamber.

When the device has a gasket and/or a manifold, the end of the magnetic stirrer located towards the top of the chamber may comprise a protrusion for reducing the frictional forces generated when the magnetic stirrer is rotated against the gasket or the manifold.

Preferably, the microchannel is fluidly connected to a downstream reservoir, which is preferably located in the block.

Preferably, the microchannel is fluidly connected to an upstream reservoir, which is preferably located in the block.

In such cases, the reservoir may not comprise a magnetic stirrer. This would be the case, for instance, when the reservoir does not contain a fluid/suspension which would settle if left.

The device may also comprise a first, base, layer; and a second layer; wherein the second layer comprises the chamber. Having the device formed of different layers allows the manufacture of the device to be simplified, since each layer can be formed separately, and then all the layers attached together to form the device.

In one example, the microchannel may be formed between the first layer and the second layer.

In some cases, the block may comprise more than one chamber, each chamber with its own magnetic stirrer; wherein the microchannel is fluidly connected to the chambers via the chamber outlets. In this way, a plurality of fluids can be separately held, and subsequently mixed in the microchannel.

The application also provides for the use of such a device, wherein the microchannel from the device is fluidly connected to a downstream reservoir, and also to an upstream reservoir;

wherein a first particle suspension is located in the chamber; and wherein an oil-based fluid is located in the upstream reservoir;

wherein the use of the device includes:

applying pressure to the first chamber, and to the upstream reservoir, to force the first particle suspension and the oil based fluid into the microchannel;

mixing the suspensions and the oil based fluid in the microchannel such that they form an emulsion which comprises a plurality of droplets, wherein at least one of the droplets encapsulates a first particle from the first particle suspension; and storing the emulsion in the downstream reservoir.

The first particle may be a cell, and the first particle suspension a cell suspension. It will be appreciated that the cell used in the suspension will vary depending on the application of the device. Preferably, the cell may include any type of biological cell which can be located in a suspension, such as but not limited to: T cells (white blood cells) and *E. Coli* cells (bacteria).

The first particle may be a bead, and the first particle suspension a bead suspension. Particularly in biological applications, the beads may preferably be between 1-20 μm in diameter; and may preferably be made of a polymer such as polycarbonate, or a hydrogel.

The oil-based fluid used will depend on the application of the device. Where the device is used to encapsulate a cell or a bead, preferably the oil-based fluid is one which exhibits good biocompatibility and which is immiscible with water, such as fluorocarbon oil. One commercially available fluorocarbon oil is Fluorinert® FC-40. The oil-based fluid may also be a hydrocarbon oil, such as decane.

To reduce the coalescence of the droplets after they have been formed, the oil-based fluid may comprise a surfactant. For fluorocarbon oil, the surfactant may comprise a fluorinated surfactant. For a hydrocarbon oil, the surfactant may comprise Tween® (ethoxylated sorbitan esters) or Span® (sorbitan esters).

In the above uses, and where the block comprises more than one chamber, wherein each chamber has its own magnetic stirrer; and wherein the microchannel is fluidly connected to the chambers via the chamber outlets:

the first particle suspension may be located in a first chamber from the more than one chamber;

a second particle suspension may be located in a second chamber from the more than one chamber;

such that use of the device includes:

applying pressure to the second chamber, to force the second particle suspension into the microchannel; and mixing the first and second particle suspensions and the oil based fluid in the microchannel such that they form an emulsion which comprises a plurality of droplets, wherein at least one of the droplets encapsulates a first particle from the first particle suspension and a second particle from the second particle suspension.

In this use, and where the first particle is a cell, and the first particle suspension is a cell suspension; the second particle may be a bead, and the second particle suspension a bead suspension.

In the above uses, the flow of fluid in the microchannel preferably has a Reynolds number of no more than 2200.

In the above uses, each suspension and the oil-based fluid are preferably pumped through the microchannel at a substantially constant rate.

Other uses for the device include encapsulating only beads or cells into droplets, and/or encapsulating other objects, such as DNA, into droplets. Other uses for the device including encapsulating the above objects, or other objects, into a non-oil based fluid(s).

In one method, the device described above may be formed using injection moulding. In one particular method, the second layer may be formed by injection moulding. The first, base, layer from the device may then be formed either by injection moulding; or formed of a plastic sheet or film, which may be fabricated by rolling/calendering or casting.

BRIEF DESCRIPTION OF THE FIGURES

The invention will now be described with reference to the accompany Figures in which:

FIG. 2a shows a cross-section view of a first embodiment device; and

FIG. 2b shows a top view of the device from FIG. 2a.

DETAILED DESCRIPTION

Figure 2:
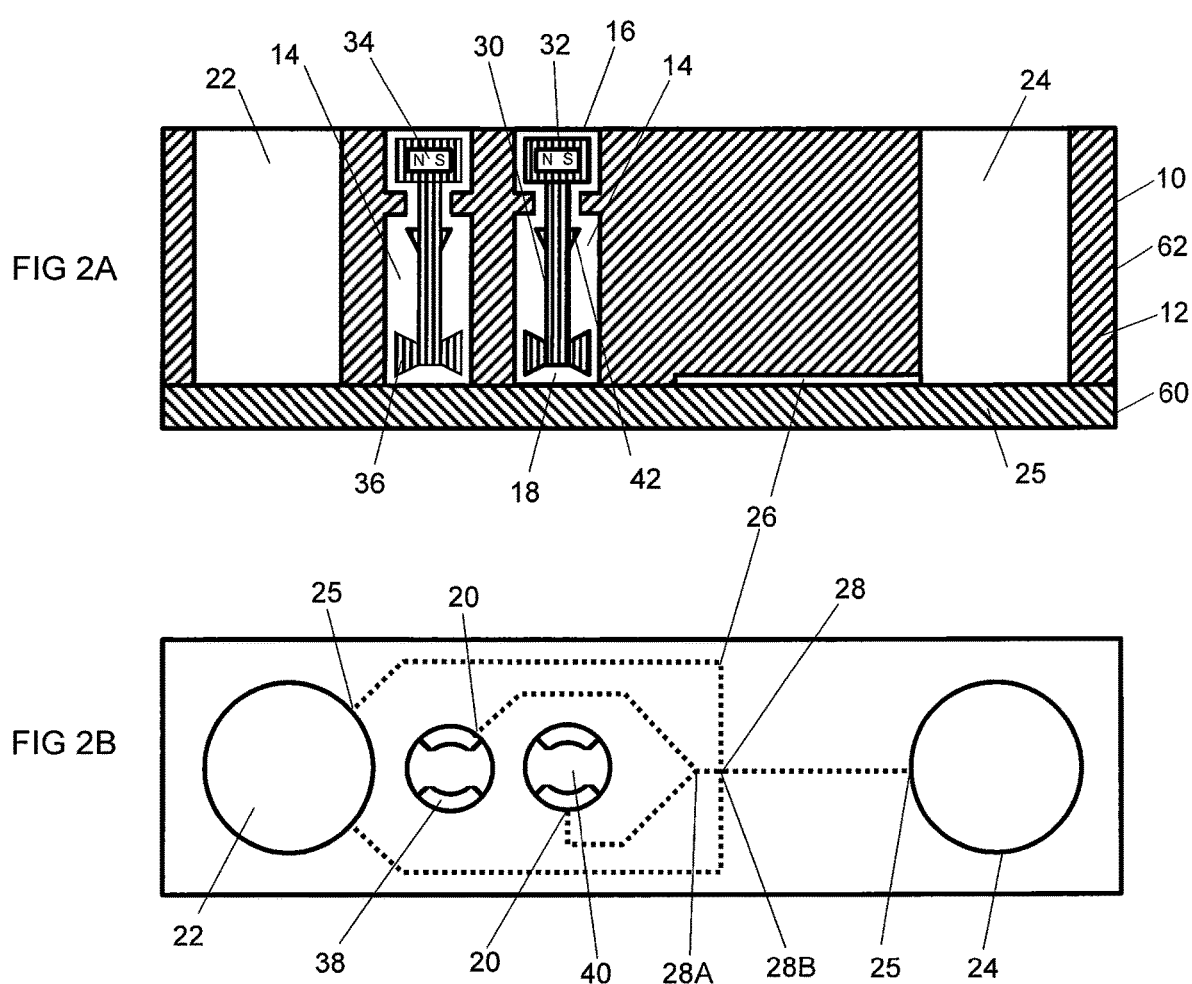

With reference to FIGS. 2a and 2b, there is shown a device 10 shaped to form a block 12. The block 12 comprises at least one cylindrical chamber 14. In this example, there are two chambers 14, each for receiving a cell/bead suspension, and each of which has an open top end 16 and a closed bottom end 18. Located at the bottom of each chamber 14 is an outlet 20 which allows fluid to escape from the chamber.

The block 12 additionally comprises an upstream reservoir 22 for storing an oil-based fluid, and a downstream reservoir 24 for storing a mixed fluid as will be described. Each of these reservoirs 22;24 has an open top end and a closed bottom end, and a fluid port 25 at their bottom end.

A microchannel 26 is fluidly connected to the upstream reservoir 22 and the outlet 20 of each chamber 14 in such a way that the oil-based fluid and the cell/bead suspensions from can be pumped to one or more mixing points 28A;2B in the microchannel 26. In FIG. 2B, the microchannel 26 comprises a first mixing point 28A where the cell/bead suspensions from the chambers 14 mix. Downstream of the first mixing point 28A is a second mixing point 28B where the mixed cell/bead suspensions further mix with the oil-based fluid from the upstream reservoir 22. Located at the downstream end of the microchannel 26 is the downstream reservoir 24, which is located on the block 12.

A magnetic stirrer 30 is suspended in each chamber 14 such that the stirrer terminates above the bottom end 18 of the chamber 14, and such that it is rotatably supported inside the chamber 14. The top end of each stirrer 30 comprises an enlarged section 32 which supports a permanent magnet 34. The bottom end of the stirrer 30 comprises vanes 36 which operate to engage with, and stir, the cell/bead suspension located inside the chamber during use of the device 10.

Towards the top end of each chamber 14 is a shelf 38 which projects radially inwardly, and which extends around a portion of the circumference of the chamber 14. The shelf 38 defines an aperture 40 through which the magnetic stirrer 30 is suspended in the chamber 14.

When suspended inside the chamber 14, the bottom end of the enlarged section 32 from the stirrer 30 rests on the top side of the shelf 38.

Preferably, the magnetic stirrer 30 comprises a snap-fit feature 42 which is operable to snap-fit past the shelf 38 when the magnetic stirrer 30 is inserted into the chamber 14, and to prevent withdrawal of the stirrer 30 out of the chamber 14.

In operation of the device 10, a cell/bead suspension is poured into each chamber 14 via its open top end 16. The magnetic stirrers 30 are then operated to prevent the cell/bead suspensions from settling inside the chambers 14. Since the magnetic stirrers 30 do not rest on the bottom of the chambers 14, the cell/beads located in the suspensions are not damaged as a result of the stirring.

An oil-based fluid is then poured into the open top end of the upstream reservoir 22.

Pressurised gas is then selectively pumped into the top end of the chambers 14 and the upstream reservoir 22 which forces the fluids located therein into the microchannel 26, past the mixing points 28A;28B, and then out into the downstream reservoir 24.

Upon the cell/bead suspensions and the oil-based fluid mixing at the mixing points 28A;28B in the microchannel 26, an emulsion is created which comprises a plurality of droplets, wherein at least one of the droplets encapsulates a cell and a bead. The resultant emulsion is stored in the downstream reservoir 24 where it can be further processed, as required.

To improve the properties of the above mentioned droplets, the device 10 is preferably operated such that the flow of fluids pumped through the microchannel 26 is laminar, and has a Reynolds number of no more than 2200. To help ensure such flow, preferably the suspensions and the oil-based fluid are pumped through the microchannel at a substantially constant rate.

Figure 1:
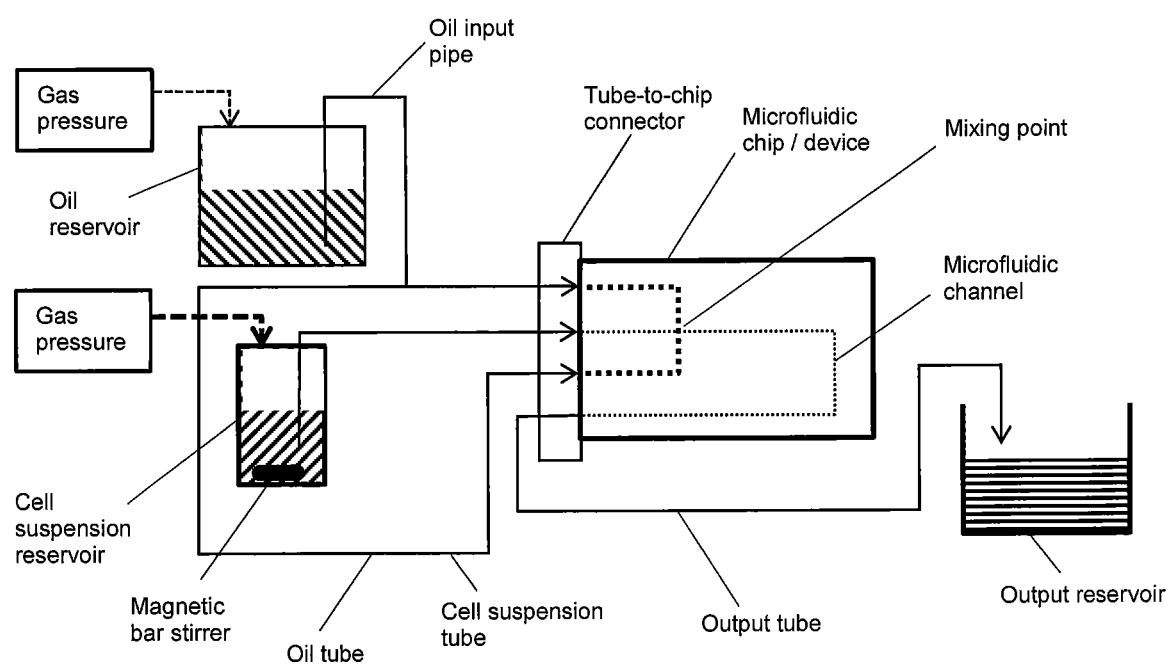
FIG. 1 shows a prior art reactor device.

Since the reservoirs 22;24 and the chambers 14 are all located on the block 12, the need for the tubes and connections as shown in FIG. 1A is removed, which means that the possibility of blockages in such tubes and connections is removed.

In the case of the block 12 shown in FIGS. 2a and 2b, the block 12 is manufactured to have a first/base layer 60 and a second layer 62 located on top of the base layer 60. The second layer 62 contains the chambers 14 and the reservoirs 22;24. The microchannel 16 is formed at the interface of the two layers 60;62.

Figure 3:
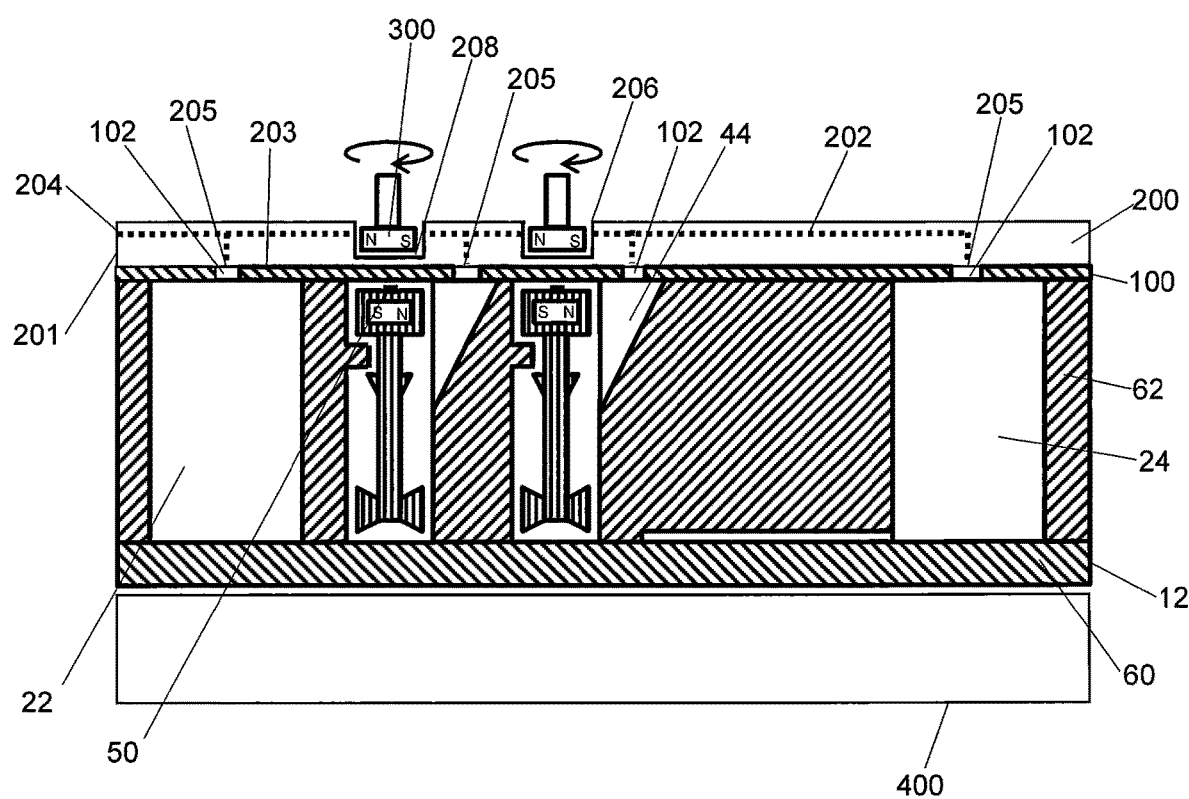
FIG. 3 shows a cross-section view of a second embodiment device.

A variant of the device shown in FIGS. 2a and 2b is shown in FIG. 3. In this variant, each chamber 14 from the block 12 comprises an enlarged portion 44 located at its open end 16. The enlarged portion 44 is shaped as a funnel, and is offset from the rotation axis of the magnetic stirrer 30, which allows a cell/bead suspension to be more easily poured into the chamber 14. In this case, the shelf 38 is not present at the portion of the circumference of the chamber 14 which comprises the funnel-shaped enlarged portion 44.

The device shown in FIG. 3 also comprises a gasket 100 for covering the top end of the block 12. The gasket 100 is preferably made of an elastomeric material such that it can be located over the top of the block 12 to create an air-tight seal between the block and the gasket. In one embodiment, the gasket 100 can be fixed to the block 12 and located using holes (not shown in the Figures) in the gasket 100 which engage with respective pins on the top surface of the block 12. In a second embodiment, features may be integrally moulded in the gasket 100 which locate with respective recesses in the block 12. The gasket comprises respective holes 102 located over the top of each of the reservoirs 22;24 and the chambers 14. In the case of the chambers 14, the hole 102 is in fluid communication with the funnel-shaped portion 44.

A manifold 200 is located on top of the gasket 100. The manifold comprises a gas channel(s) 202 which has at least one gas inlet 204 located on one side 201 of the manifold 200. The gas channel 202 also comprises a series of gas outlets 205 located on the bottom surface 203 of the manifold 200. The top surface 206 of the manifold 200 comprises a series of indentations 208 for receiving drive magnets 300 which cause the magnetic stirrers 30 to rotate during use of the block 12 as will be described.

To minimise the amount of friction generated between the gasket 100 and the magnetic stirrers 30 when they rotate, the top end of each magnetic stirrer 30 preferably comprises a raised protrusion 50 as shown in FIG. 3.

In operation of the device shown in FIG. 3, a cell/bead suspension is poured into each chamber 14 via the funnel-shaped enlarged portions 44. An oil-based fluid is then poured into the open top end of the upstream reservoir 22. The gasket 100 is then secured over the top of the block 12, and the manifold 200 then located on top of the gasket 100, such that the gasket is compressed between the manifold 200 and the block 12, as shown in FIG. 3. In this position, operation of the drive magnets 300 in the indentations 208 from the manifold 200 causes the magnetic stirrers 30 to rotate.

The cell/bead suspensions and the oil-based fluid can then be pumped around the block 12 by pumping gas, as required, into the gas inlet(s) 202, through the gas channel 202 and the gas outlets 205, and into the top end of the chambers 14 and the reservoirs 22.

During operation of the device shown in FIG. 3, the bottom of the block 12 may be positioned on an interface 400, which may comprise a temperature controlling means for affecting the temperature of the block. The interface 400 may also comprise sensors for measuring a property of either the block 12, and/or fluid located inside of the block 12. The interface 400 may also comprise a user interface for allowing operational control of the drive magnets 300; manifold 200; gasket 100; and/or the block 12. In one operation, the user interface may be linked to illumination means located underneath the reservoirs and chambers, such that the user interface can indicate which of these the end user should fill by illuminating them from below.

Various modifications can be made to the above devices as will be readily apparent to the skilled person.

For instance, it will be appreciated that the gas channel(s) 202 located in the manifold 200 may be configured such to allow a gas or gases to be selectively dispensed into each reservoir 22;24 and/or each chamber 14.

It will also be appreciated that the rotational speed of each magnetic stirrer 30 can be individually controlled, as required, depending on the fluid that is to be inserted into each chamber 14.

Rather than have the block 12 formed of two layers 60;62, the block 12 may instead be formed of three layers, with an intermediary layer 64 located between the first layer 60 and the second layer 62. An example of such a block 12 is shown in the device from FIG. 4. In this device, the second layer 62 contains the chambers 14 and the reservoirs 22;24, and the microchannel 16 is formed at the interface of the first layer 60 and the intermediary layer 64. The outlet 20 from each chamber 14, and the fluid port into each reservoir 22;24, then extends through the intermediary layer 64 to connect these chambers/reservoirs to the microchannel 28.

Where required, a recess 68 may be provided in a top/bottom surface of any of the layers 60;62;64 to allow adhesive to be applied therein for securing two neighbouring layers together.

Figure 4:
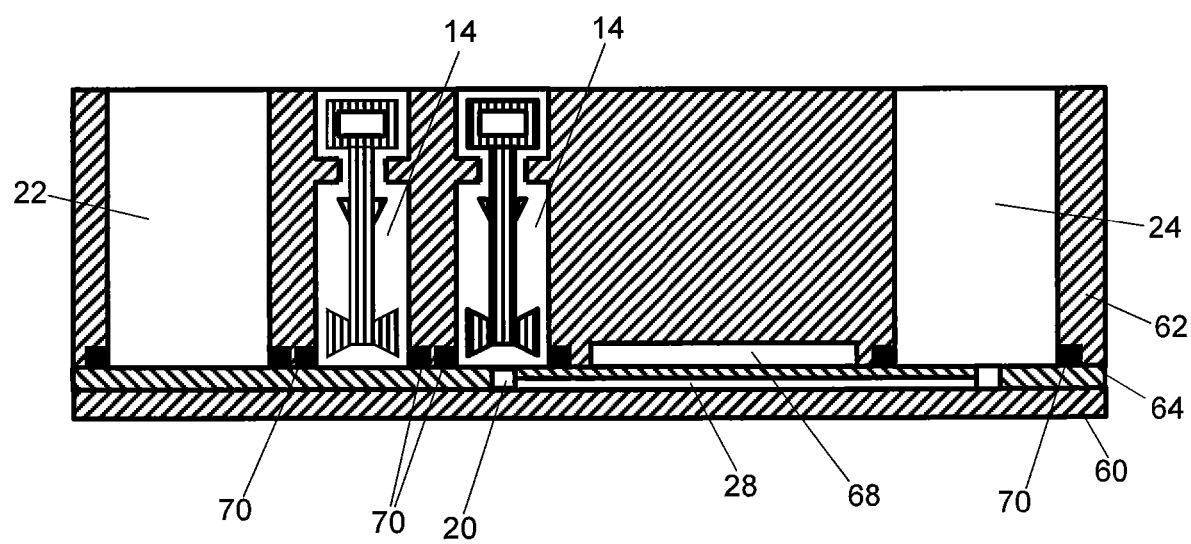
FIG. 4 shows a cross-section view of a third embodiment device.

As also shown in FIG. 4, seals 70 may also be provided at the interface between any two neighbouring layers where fluid is present at the interface.

Figure 5:
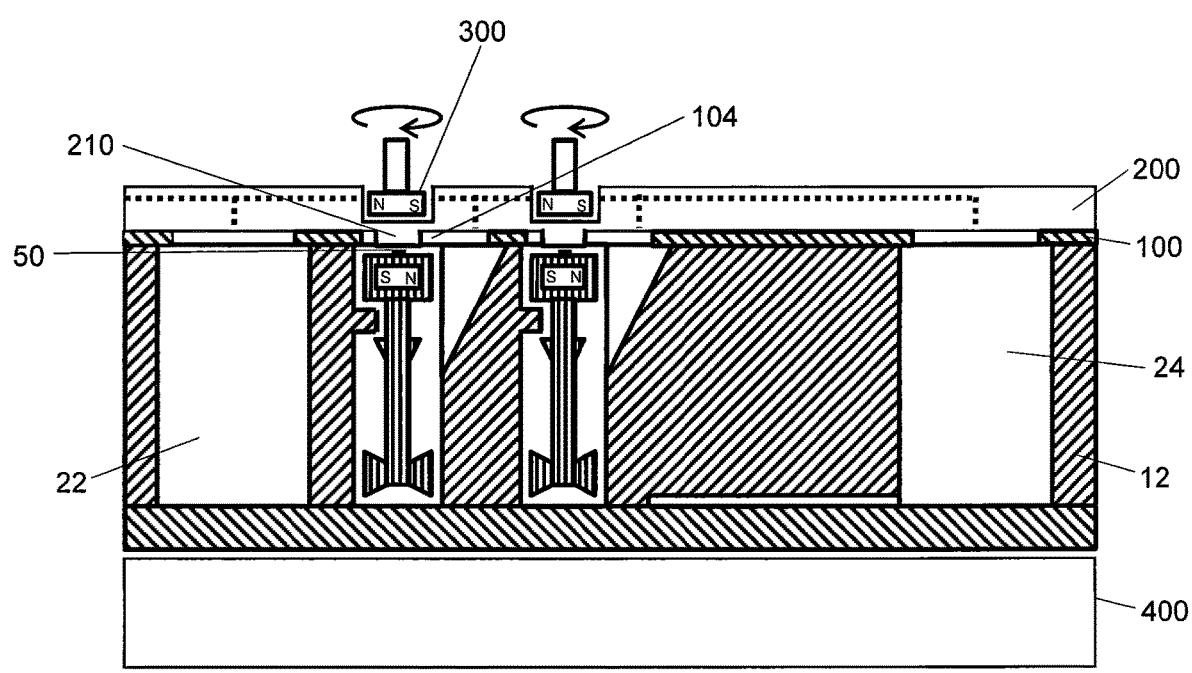
FIG. 5 shows a cross-section view of a fourth embodiment device.

In relation to the raised protrusion 50 on the magnetic stirrer 30, rather than this protrusion 50 rotate against the gasket 100, the protrusion 50 could instead extend through a hole in the gasket 100 and rotate directly against the manifold 200. Alternatively, as shown in FIG. 5, a raised portion 210 of the manifold 200 may extend through a hole 104 in the gasket 100 to allow the protrusion 50 to rotate against the manifold 200.

Particularly when the devices described herein are made of plastic, the devices may be manufactured using injection moulding. In one particular example, the second layer 62 may be formed by injection moulding, and the first layer 60 and the intermediary layer 64 either formed by injection moulding (which may include the use of an embossing process), or formed from a plastic sheet or film, which may be fabricated by rolling/calendering or casting.

Rather than supply a positive gas pressure to the top end of the chambers 14 and the upstream reservoir 22 to force fluids located therein through the microchannel 26, it will also be appreciated that a negative pressure or vacuum could be supplied via the gas port 205 located at the top end of the downstream reservoir 24, such to draw fluids through the microchannel 26.

It will also be appreciated that the general shape of the block 12, and both the location and shape of the reservoirs 22;24 and/or chambers 14 within the block 12, can be modified as required depending on the application of the block 12, so long as it achieves its function of accommodating the reservoirs 22;24 and/or the chambers 14 in a unitary housing. For example, the sides of the block 12 may be slanted or curved, rather than straight as shown in FIGS. 2a, 2b, 3 and 4. In another example, the shape of the reservoirs 22;24 and/or the chambers 14 may vary across their length.

The invention claimed is:

1. A method of using a device, the device comprising a block that includes a chamber having a top, a bottom, and a chamber outlet at the bottom of the chamber, wherein a magnetic stirrer is suspended in the chamber, wherein the magnetic stirrer terminates above the bottom of the chamber, and is rotatably supported inside the chamber such that the magnetic stirrer does not come into contact with any part of a lower portion of the chamber, and wherein a microchannel is fluidly connected to the chamber via the chamber outlet and to a downstream reservoir and also to an upstream reservoir, wherein a first particle suspension is located in the chamber, and wherein an oil-based fluid is located in the upstream reservoir the method comprising:

applying pressure to the chamber, and to the upstream reservoir, to force the first particle suspension and the oil-based fluid into the microchannel;

mixing the suspension and the oil-based fluid in the microchannel such that they form an emulsion which comprises a plurality of droplets, wherein at least one of the droplets encapsulates a first particle from the first particle suspension; and storing the emulsion in the downstream reservoir.

2. The method according to claim 1, wherein the first particle is a cell, and the first particle suspension is a cell suspension.

3. The method according to claim 1, wherein the first particle is a bead, and the first particle suspension is a bead suspension.

4. The method according to claim 1, wherein the block comprises a plurality of chambers, each chamber with its own magnetic stirrer, wherein the microchannel is fluidly connected to the plurality of chambers via respective chamber outlets, wherein the first particle suspension is located in a first chamber of the plurality of chambers, wherein a second particle suspension is located in a second chamber of the plurality of chambers, wherein the method further comprises:

applying pressure to the second chamber, to force the second particle suspension into the microchannel; and mixing the first and second particle suspensions and the oil-based fluid in the microchannel such that they form an emulsion which comprises a plurality of droplets, wherein at least one of the droplets encapsulates a first particle from the first particle suspension and a second particle from the second particle suspension.

5. The method of claim 4, wherein the second particle is a bead, and the second particle suspension is a bead suspension.

* * * * *